(12) United States Patent
Shah et al.

(10) Patent No.: US 8,093,064 B2
(45) Date of Patent: Jan. 10, 2012

(54) METHOD FOR USING MAGNETIC PARTICLES IN DROPLET MICROFLUIDICS

(75) Inventors: Gaurav Jitendra Shah, Los Angeles, CA (US); Chang-Jin Kim, Beverly Hills, CA (US)

(73) Assignee: The Regents of the University of California, Oakland, CA (US)

( * ) Notice: Subject to any disclaimer, the term of this patent is extended or adjusted under 35 U.S.C. 154(b) by 252 days.

(21) Appl. No.: 12/465,935

(22) Filed: May 14, 2009

(65) Prior Publication Data

US 2009/0283407 A1 Nov. 19, 2009

Related U.S. Application Data

(60) Provisional application No. 61/053,558, filed on May 15, 2008.

(51) Int. Cl.
*G01N 25/08* (2006.01)
(52) U.S. Cl. ........................................ 436/150; 210/767
(58) Field of Classification Search .................. None
See application file for complete search history.

(56) References Cited

U.S. PATENT DOCUMENTS

| | | |
|---|---|---|
| 2003/0205632 A1 | 11/2003 | Kim et al. |
| 2006/0164490 A1 | 7/2006 | Kim et al. |
| 2007/0023292 A1 | 2/2007 | Kim et al. |
| 2008/0124252 A1 | 5/2008 | Marchand et al. |
| 2009/0014394 A1 | 1/2009 | Yi et al. |
| 2009/0042319 A1 | 2/2009 | De Guzman et al. |
| 2009/0280251 A1 | 11/2009 | De Guzman et al. |

FOREIGN PATENT DOCUMENTS

| | | |
|---|---|---|
| WO | WO 2006/127451 | 11/2006 |
| WO | WO 2006/127451 A2 | 11/2006 |

OTHER PUBLICATIONS

Raccurt, O. et al. On the influence of surfactants in electrowetting systems, 2007, Journal of Micromechanics and Microengineering, vol. 17, pp. 2117-2223.*
Al-Rubeai, Mohamed et al., The effect of Pluronic F-68 on hybridoma cells in continuous culture, Appl Microbiol Biotechnol (1992) 37:44-45.
Olsvik, Orjan et al., Magnetic Separation Techniques in Diagnostic Microbiology, Clinical Microbiology Reviews, (Jan. 1994), 7 (1), 43-54.

(Continued)

*Primary Examiner* — Yelena G Gakh
*Assistant Examiner* — Robert Xu
(74) *Attorney, Agent, or Firm* — Vista IP Law Group LLP

(57) ABSTRACT

Methods of utilizing magnetic particles or beads (MBs) in droplet-based (or digital) microfluidics are disclosed. The methods may be used in enrichment or separation processes. A first method employs the droplet meniscus to assist in the magnetic collection and positioning of MBs during droplet microfluidic operations. The sweeping movement of the meniscus lifts the MBs off the solid surface and frees them from various surface forces acting on the MBs. A second method uses chemical additives to reduce the adhesion of MBs to surfaces. Both methods allow the MBs on a solid surface to be effectively moved by magnetic force. Droplets may be driven by various methods or techniques including, for example, electrowetting, electrostatic, electromechanical, electrophoretic, dielectrophoretic, electroosmotic, thermocapillary, surface acoustic, and pressure.

14 Claims, 6 Drawing Sheets

OTHER PUBLICATIONS

Liu, Feng et al., Effect of Non-Ionic Surfactants on the Formation of DNA/Emulsion Complexes and Emulsion-Mediated Gene Transfer, Pharmaceutical Research, (1996), 13 (11), 1642-1646.

Weber, Christoph et al., Specific Blood Purification by Means of Antibody-Conjugated Magnetic Microspheres, New York (1997), pp. 371-374.

Cho, Sung Kwon et al., Creating, Transporting, Cutting, and Merging Liquid Droplets by Electrowetting-Based Actuation for Digital Microfluidic Circuits, J. Mems., (Feb. 2003), 12 (1), 70-80.

Furdui, Vasile et al., Immunomagnetic T cell capture from blood for PCR analysis using microfluidic systems, Lab Chip (2004), 4, 614-618.

Shah, Gaurav J. et al., Meniscus-Assisted Magnetic Bead Trapping on Ewod-Based Digital Microfluidics for Specific Protein Localization, Transducers & Eurosensors (2007), 707-710.

Ettenauer, Marion et al., Magnetic Fluorescent Microparticles as Markers for Particle Transfer in Extracorporeal Blood Purification, Biomacromoleculres (2007), 8 (12), 3693-3696.

Shah, Gaurav J. et al., Meniscus-Assisted High-Efficiency Magnetic Collection and Separation for EWOD Droplet Microfluidics, J. MEMS (Apr. 2009), 18 (12), 363-375.

Alrubeai, M. et al., The Effect of Pluronic F-68 on Hybridoma Cells in Continuous Culture, Applied Microbiology and Biotechnology, vol. 37, pp. 44-45, Apr. 1992.

Furdui, V.I. et al., Immunomagnetic T Cell Capture from Blood for PCR Analysis Using Microfluidic Systems, Lab on a Chip, vol. 4, pp. 614-618, 2004.

Liu, F et al., Effect of Non-Ionic Surfactants on the Formation of DNA/emulsion Complexes and Emulsion-mediated Gene Transfer, Pharmaceutical Research, vol. 13, pp. 1642-1646, Nov. 1996.

Weber, C. et al., Specific Blood Purification by Means of Antibody-Conjugated Magnetic Microbeads, in Specific and Clinical Applications of Magnetic Carriers, U. Hafeli and W. Schut, Eds. New York: Pergamon Press, 1997, 371-8.

\* cited by examiner

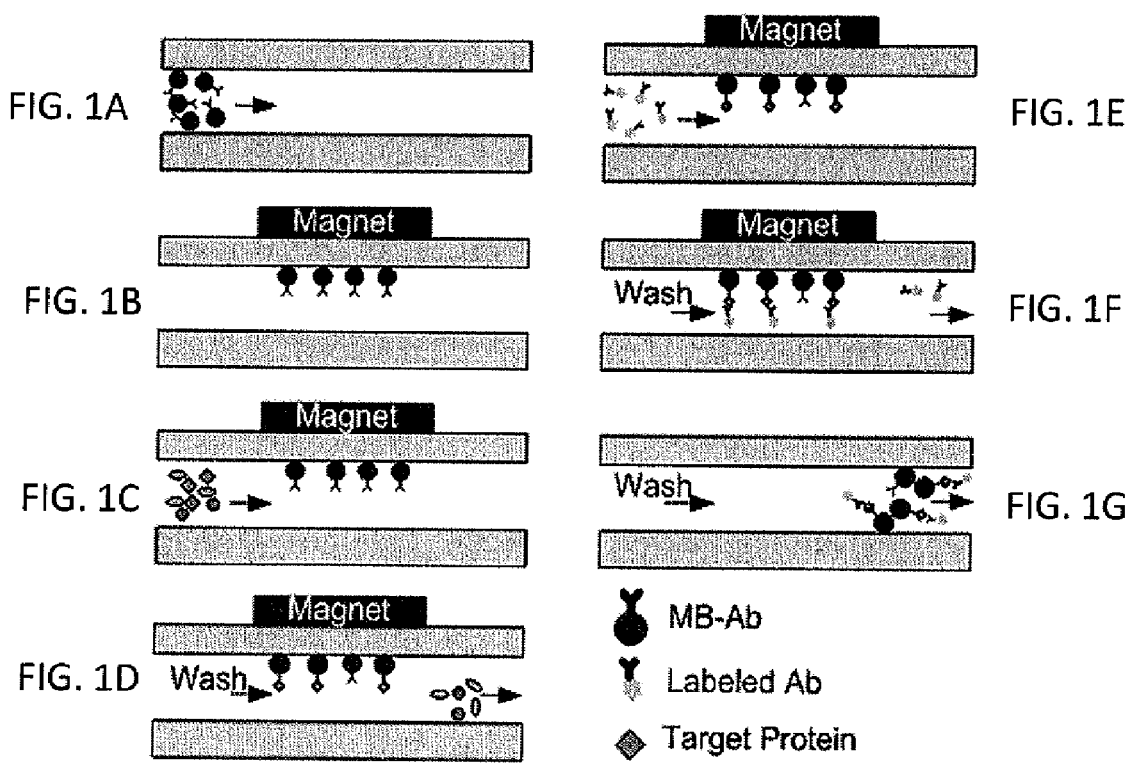
Prior Art

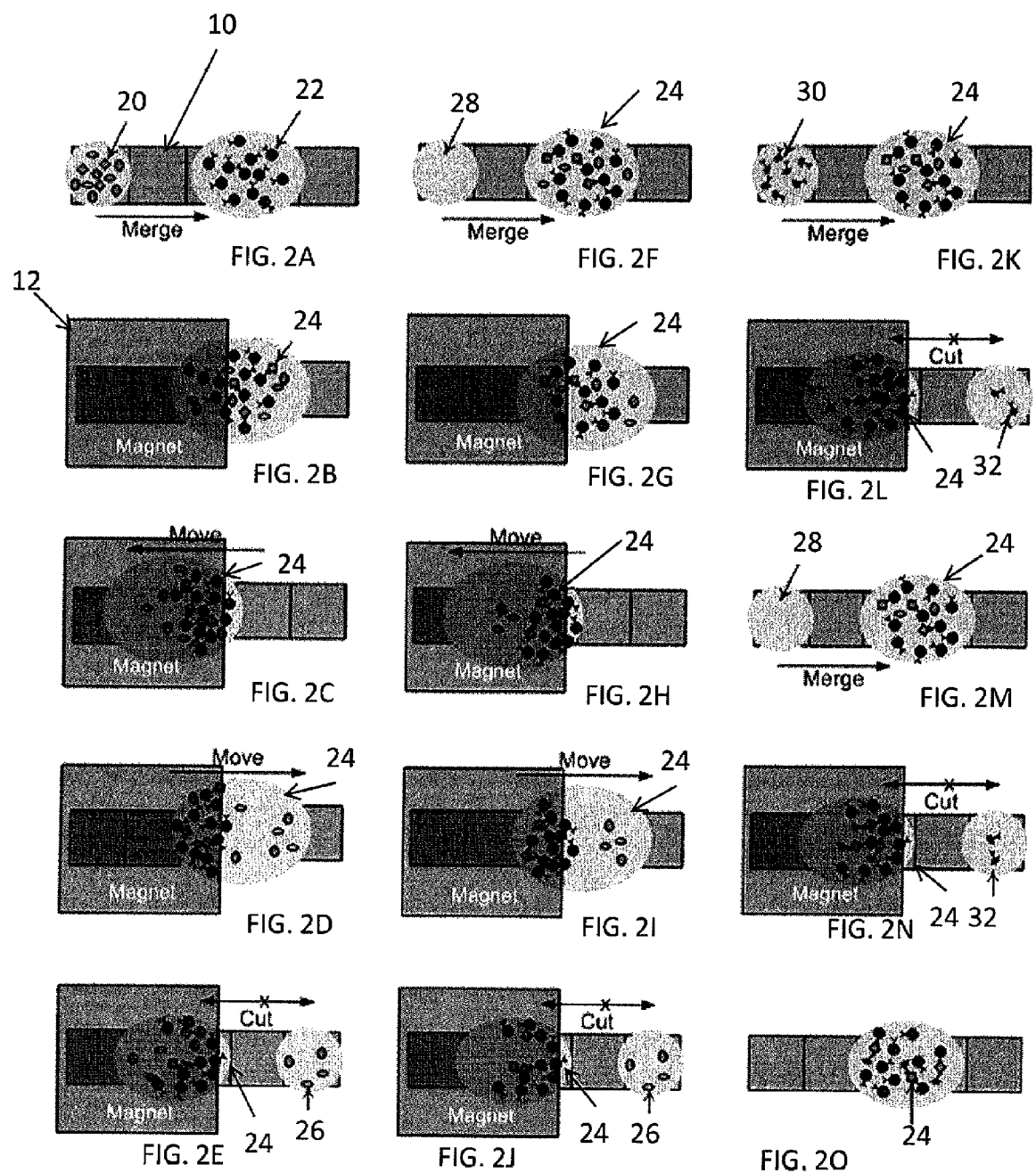

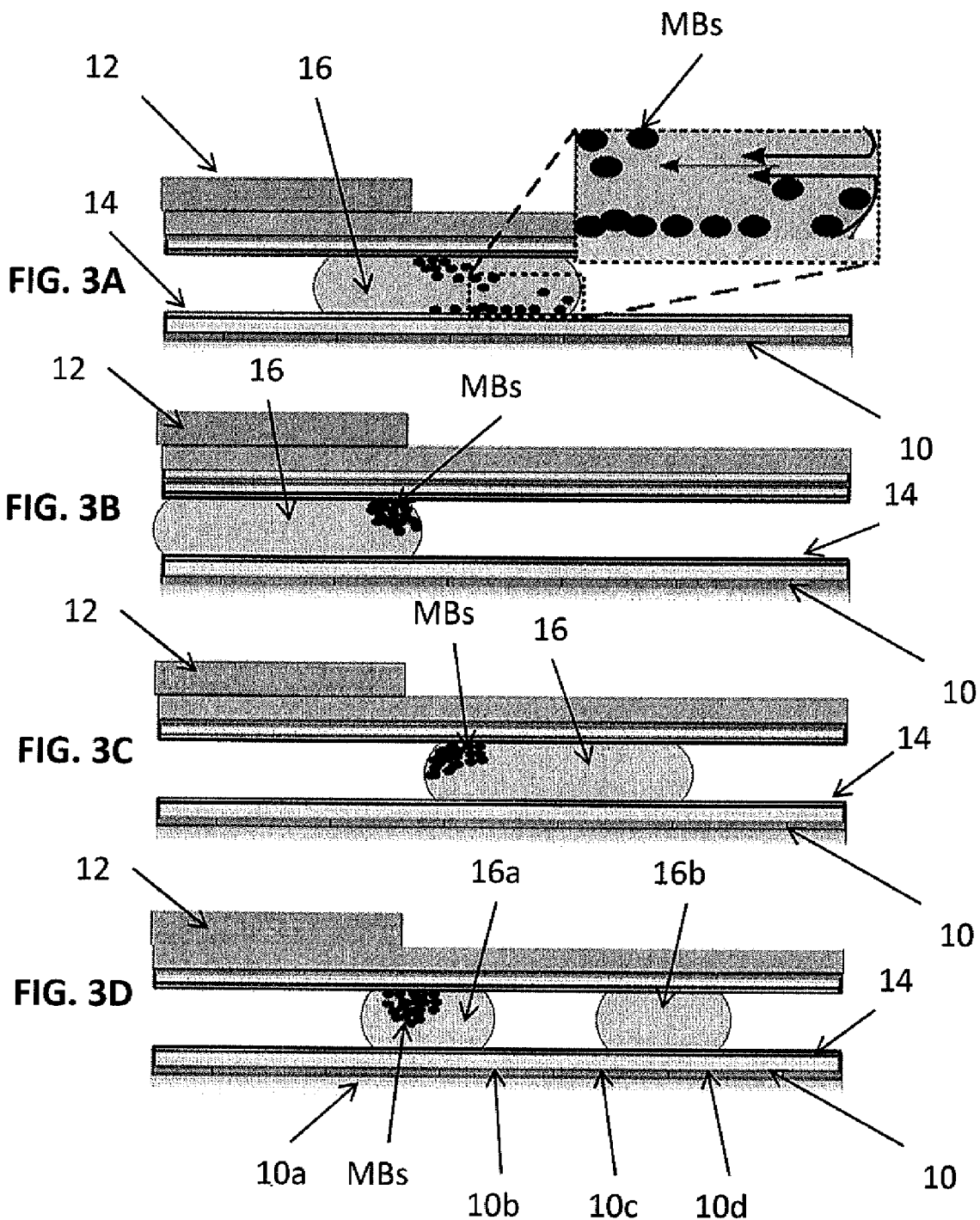

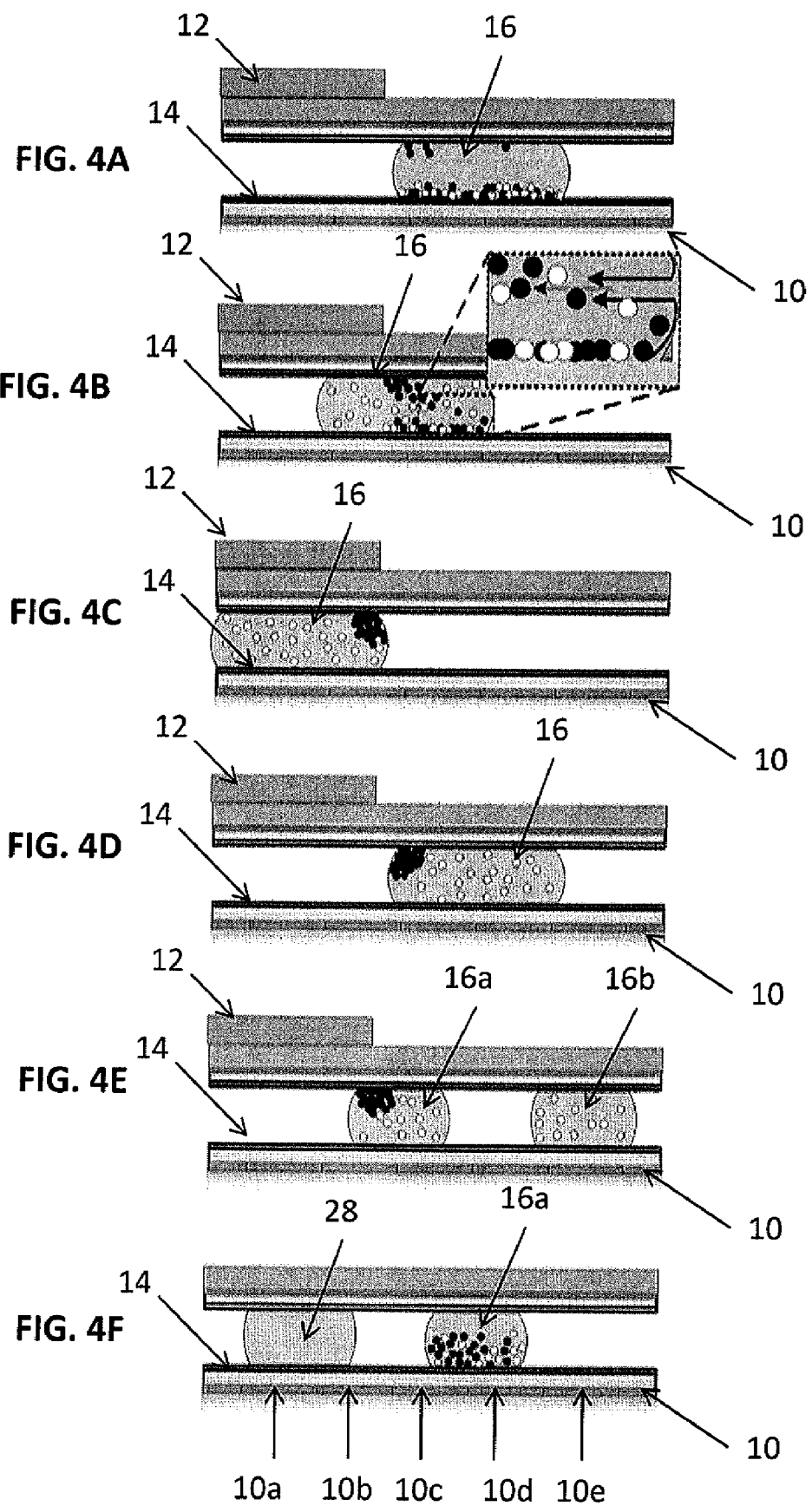

US 8,093,064 B2

METHOD FOR USING MAGNETIC PARTICLES IN DROPLET MICROFLUIDICS

REFERENCE TO RELATED APPLICATIONS

This Application claims priority to U.S. Provisional Patent Application No. 61/053,558 filed on May 15, 2008. U.S. Provisional Patent Application No. 61/053,558 is incorporated by reference as if set forth fully herein.

STATEMENT REGARDING FEDERALLY SPONSORED RESEARCH AND DEVELOPMENT

This invention was made with Government support of Grant No. NCC21364 awarded by the National Aerospace and Space Administration (NASA) and Grant No. AIO65359 awarded by the National Institutes of Health (NIH). The Government has certain rights in this invention.

FIELD OF THE INVENTION

The field of the invention generally relates to droplet-based (also called digital) microfluidic devices and methods. More specifically, the field of the invention relates to the use of magnetic particles or beads in conjunction with droplet microfluidic operations. The method may be used to assist in the collection and positioning of magnetic particles or beads, including superparamagnetic and immunomagnetic ones.

BACKGROUND OF THE INVENTION

Target concentration and separation using magnetic beads (hereinafter MBs), for their unique advantages, have been gaining popularity in biochemical practice including microfluidics. These techniques may be used for purification of bodily fluids. See e.g., O. Olsvik, T. Popovic, E. Skjerve, K. S. Cudjoe, E. Homes, J. Ugelstad, and M. Uhlen, "Magnetic Separation Techniques in Diagnostic Microbiology", *Clinical Microbiology Reviews*, Vol. 7, pp. 43-54, 1994. Still others have employed magnetic to isolate specific cells from blood samples. See e.g., V. I. Furdui and D. J. Harrison, "Immunomagnetic T Cell Capture From Blood For PCR Analysis Using Microfluidic Systems," Lab on a Chip, Vol. 4, pp. 614-618, 2004. In a typical procedure, the MBs are held back (i.e., trapped) on a surface position by magnetic force, while a fluid passes by or over the MBs. When the fluid contains targets, these targets build on the MB surface and thus become concentrated, as the MBs have a special affinity to the targets. When the fluid is exchanged with a wash fluid, all the particles and species except the targets on the MBs are washed away and separated (i.e., the targets on the MBs are purified). In the case of a typical prior art immunoassay, the target is a protein, and the MBs are conjugated with antibody (Ab). This prior art technique is described in FIGS. 1A-G. As seen in FIG. 1A, MBs conjugated with Ab are introduced as a suspension in a liquid. As seen in FIG. 1B, the antibody (Ab)-conjugated MBs are then trapped at a location on the surface of the device using an external magnet.

Next, as seen in FIG. 1C, a sample of proteins, that includes both the target protein and non-target proteins, are permitted to flow into the device and past the antibody (Ab)-conjugated MBs trapped at the surface of the device. Referring now to FIG. 1D, target proteins bind to the Ab that is conjugated to the MBs. Unbound non-target proteins are washed away with a wash solution.

Optionally, as seen in FIG. 1E, labeled antibody (Ab) is then permitted to flow into the device. The labeled Ab will then bind to those Ab-conjugated MBs that are already bound with target protein. In this regard, the labeled Ab will sandwich the target protein. The labeled Ab may include a fluorescent label that fluoresces in response to incident radiation.

Unbound labeled Ab is then washed away as illustrated in FIG. 1F. Detection or analysis or any other processes may optionally be performed on the sample. The magnet may then be removed as illustrated in FIG. 1G, and the MBs and targets (as well as, optionally, their conjugated labels) may then be washed away from the surface of the device, for further processes or operations with this purified sample.

The above prior art process applies to conventional conditions, where liquids move between containers in bulk or flow continuously within channels. However, when the fluids are handled in digitized packets (e.g., droplets), as in droplet-based digital microfluidics, the above-noted process does not work because of the existence of liquid-gas or liquid-liquid interfaces. In particular, as the droplet passes across the position where the MBs are to be held, the passing meniscus pulls the MBs away from the surface with a force that is orders-of-magnitude stronger than the magnetic force. The magnetic force produced by even with the strongest magnet available is not strong enough to counter the interfacial force in the scale of typical MBs. Because of this strong interfacial force (i.e., surface tension) of the meniscus of the droplet, the MBs cannot be magnetically trapped on the surface against a droplet sliding across the surface. Instead, the MBs get carried away with the moving droplet. The interfacial force is also much stronger than the short range surface forces (e.g., van der Waals force) which act on MBs in contact with the device surface. This is true for commercially available "naked" MBs (e.g. polystyrene beads) as well as antibody-conjugated MBs often used for cell selection and protein enrichment, among many other cases. This, the prior art process envisioned in FIGS. 1A-1G is inapplicable for droplet-based microfluidic applications.

SUMMARY OF THE INVENTION

In a first aspect of the invention, a method of manipulating magnetic particles disposed within a droplet that is located on or in close proximity to a surface is provided. The method includes sweeping a meniscus of the droplet so as to lift the magnetic particles off the surface and applying a magnetic field to the droplet containing the magnetic particles, the magnetic field concentrating the magnetic particles in a region of the droplet. The droplet is then cut at a location outside of the region containing the magnetic particles.

In a second aspect of the invention, a method of manipulating magnetic particles within a droplet located on or in close proximity to a surface includes adding a surfactant to at least one of the droplet, magnetic particles, or the surface and applying a magnetic field to the droplet containing the magnetic particles, the magnetic field concentrating the magnetic particles in a region of the droplet. The droplet is then cut at a location outside of the region containing the magnetic particles.

In another aspect of the invention, a method of concentrating a target using magnetic particles within a droplet includes merging a droplet containing the target with a droplet containing magnetic particles having a specific affinity to said target. A magnetic field is then applied to the merged droplet. The merged droplet is then moved relative to the magnetic field to concentrate magnetic particles containing bound target in a region of the merged droplet and the merged droplet is then cut at a location outside of the region containing the magnetic particles containing bound target.

While the invention is described herein as having particular applicability for increasing the concentration of a target species, the invention may also be used to reduce the concentration of non-target species.

BRIEF DESCRIPTION OF THE DRAWINGS

FIGS. 1A-1G illustrate a prior art method of using magnetic beads for concentrating and purifying a target in an immunoassay using a channel-based, continuous-flow microfluidic device.

FIG. 2A-2O illustrate a method of using meniscus-assisted trapping of MBs applied to an immunoassay using a microfluidic device employing digital microfluidics (e.g., EWOD driving of droplets).

FIGS. 3A-3D illustrate a cross-sectional view of a microfluidic device employing digital microfluidics (e.g., EWOD driving of droplets) along with a permanent magnet to collect MBs.

FIGS. 4A-4F illustrate a cross-sectional view of a microfluidic device employing digital microfluidics (e.g., EWOD driving of droplets) along with a permanent magnet to increase the concentration of MBs in a droplet containing a mixture of MBs (dark circles) and non-MBs (light circles).

DETAILED DESCRIPTION OF THE ILLUSTRATED EMBODIMENTS

Figure 5A:
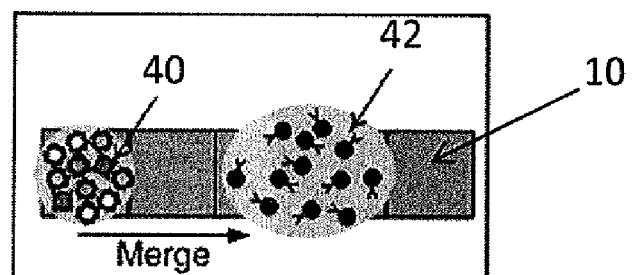
FIGS. 5A-5E illustrate a method of using meniscus-assisted trapping of MBs applied to cell enrichment using a microfluidic device employing digital microfluidics (e.g., EWOD driving of droplets).

FIGS. 2A-2O illustrate a method of using meniscus-assisted trapping of MBs applied to an immunoassay using a microfluidic device employing digital microfluidics. While MBs are illustrated in FIGS. 2A-2O, the method applies to any magnetic particles including MBs. The term "magnetic particles" would thus encompass MBs. In the immunoassay application of FIGS. 2A-2O, a plurality of electrodes 10 forming an electrowetting-on-dielectric (EWOD) device are used to manipulate the various droplets described in more detail herein. Five (5) separate electrodes 10 are illustrated in FIGS. 2A-2O although any number can be used in accordance with the methods described herein. Generally, an EWOD device is formed using a plurality of separate driving electrodes 10. These driving electrodes may be formed as a plurality of square or other shaped electrodes with adjacent boundaries (e.g., 1-1.2 mm width) that are driven by an applied alternating current (AC) voltage (e.g., 70 $V_{AC}$ at 1 KHz). Electronic control for the activation of the various electrodes may be accomplished using various off-chip circuitry. For example, electronic control may be provided using LabVIEW software in conjunction with a digital I/O device.

EWOD-based devices may be fabricated using known microfabrication techniques. Generally, it consists of a layer of conductive material patterned in the form of electrodes 10 that is covered by layers of dielectric (e.g. silicon dioxide, silicon nitride, parylene) and hydrophobic (e.g. Teflon®, Cytop®) materials. By controlling the voltage at each respective electrode 10, the surface tension (surface energy) can be reversibly manipulated, causing fluid to move in the energetically favorable direction. For example, droplets can be created, merged, moved, cut, etc. in a reprogrammable fashion using the appropriate actuation sequence. EWOD-based devices are able to create, transport, cut and merge droplets in a microfluidic environment. For example, the fundamental operations and structures used in EWOD-based devices is described in Cho et al., "Creating, Transporting, Cutting, and Merging Liquid Droplets by Electrowetting-Based Actuation for Digital Microfluidic Circuits," Journal of Microelectromechanical Systems, Vol. 12, No. 1, February 2003, pp. 70-80, which is incorporated by reference herein. The aforementioned reference describes common configurations for EWOD although other EWOD configurations may also be used (e.g., coplanar EWOD, EWOD with ground wire, etc.).

In addition, it should be understood that while the methods described herein have principally been illustrated having EWOD-based driving schemes, other methods of creating, transporting, mixing, and cutting of droplets may be used. For example, besides the electrowetting force, other forces that can be used in a digital or droplet-based device include electrostatic forces, electromechanical forces, electrophoretic forces, dielectrophoretic forces, electroosmotic forces, thermocapillary forces, surface acoustic forces, or even pressure forces. Devices operating on these schemes are contemplated to fall within the scope of the invention.

Referring to FIG. 2A, a sample droplet 20 containing target proteins (square-shaped elements in FIG. 2A) is manipulated using the EWOD electrodes 10 to merge with a droplet 22 containing MBs conjugated with antibody or Ab. The droplet 22 complex of MBs and Ab (MB-Ab) is merged with the sample droplet 20 containing target proteins and incubated to allow specific binding between the target protein and its respective Ab. While this example illustrates target proteins, the target species may include other simple or complex molecules or even whole cells. With reference to FIG. 2B, a magnet 12 is brought near the merged droplet 24 containing the target proteins and the MB-Ab. The magnet 12 may be formed from a permanent magnet such as, for instance, a rare earth magnet or it may be formed from an electromagnetic that may be selectively turned on and off via conventional control circuitry. In the case of a permanent magnet, a suitable rare earth magnet may be formed from NdFeB. In FIG. 2B, the MBs that are suspended in the droplet 24 move toward the magnet 12. However, many MBs are brought into contact with the device surface (the surface overlying the electrodes 10) by the vertical component of the magnetic force, or gravity, e.g., during incubation. Once MBs contact this surface, the magnetic force from the magnet 12 is ineffective in moving MBs against opposing surface forces. As such, no meaningful portion of the droplet 24 can be made free of MBs, and the wash-steps by droplet cutting are inefficient.

The presently described method leverages the powerful interfacial forces caused by the moving meniscus of the droplet 24 to sweep the MBs off the surface (or MBs in close proximity to the surface) overlying the electrodes 10 and into the droplet, thereby enabling the magnetic force from the magnet 12 to move them to one side. As seen in FIGS. 2C and 2D, this is achieved by moving the droplet 24 back and forth. The droplet 24 may be moved back and forth a plurality of times or, alternatively, a single back and forth movement may be sufficient to segregate a meaningful amount of MBs to one side of the droplet 24. In this example, the EWOD electrodes 10 located on or underneath the surface of the device are used to move the droplet back and forth. It should be appreciated that the various droplets that are described herein may be formed from either a liquid or a gas. The meniscus of the various droplets may define a liquid-liquid interface or a gas-liquid interface depending on the application.

Now referring to FIG. 2E, once a significant region of the droplet 24 is cleared of MBs by the magnetic force of magnet 12, the droplet 24 is cut using the electrodes 10 to remove the unbound (i.e., non-target) proteins. The cut droplet 26 contains the unbound proteins while the now smaller droplet 24 contains the MBs along with the target proteins. The particular location where the droplet 24 is cut can be controlled by the underlying electrodes 10. Generally, the droplet 24 is cut at a location that is outside the region containing the MBs. To ensure that nearly all the unbound proteins or non-target proteins are washed away, an optional wash process is used. For example, FIG. 2F illustrates a droplet 28 containing a wash or buffer solution that is merged with the portion of droplet 24 that contains the MBs. The now merged droplet which is illustrated in FIG. 2G is then moved back and forth as previously described. This movement is illustrated in FIGS. 2H and 2I. MBs accumulate on one side of the droplet near the magnet 12 while unbound proteins remain outside this region. With reference to FIG. 2J, the droplet is then cut as described above leaving a cut droplet 26 containing the unbound proteins which can then be removed from the device.

With reference to FIG. 2K, a droplet 30 containing a labeled antibody Ab is introduced and merged into the droplet 24 containing the MBs and the target protein. The labeled Ab may include, for example, fluorescently or enzymatically Ab. The labeled Ab is incubated with the droplet 24 so as to "sandwich" the target protein between its two Abs (i.e., the Ab on the MBs and the Ab on the label). As seen in FIG. 2L, the MBs are again collected and trapped using the meniscus sweeping technique as described above while the unbound labeled Abs are removed in a cut droplet 32. As before, one or more optional wash steps may be performed using a wash or buffer droplet 28. FIG. 2M illustrates a wash droplet 28 that is merged with the remaining droplet 24 containing the MBs and the bound labeled Abs. This merged droplet is then moved back and forth as described above to sweep the MBs to one side of the droplet with the aid of the magnet 12. The droplet 24 is then cut using the EWOD electrodes 10 to produce a cut droplet 32 having unbound labeled Ab therein. The remaining droplet 24 seen in FIG. 2O contains concentrated target proteins sandwiched between the MB-Ab and labeled Ab and may be moved to the detection site for further analysis and/or processing.

FIGS. 3A-3D illustrate a cross-sectional view of a microfluidic device employing digital EWOD microfluidics along with a permanent magnet to collect MBs. This device was configured as a parallel plate EWOD device. Lithographic thin-film microfabrication processes were used to fabricate the parallel-plate EWOD device. In particular, square EWOD driving electrodes of 1-1.2 mm width were defined from an indium tin oxide (ITO) (140 nm) layer over a 700 μm-thick glass substrate (TechGophers Corporation). Cr/Au (~15/150 nm) was deposited and patterned to define the contact pads and electrode labels for easier visualization. Next, a silicon nitride layer (~1000 nm) was deposited using plasma-enhanced chemical vapor deposition (PECVD) and patterned to define the dielectric layer. A Cytop (Asahi, Inc.) layer (~1000 nm) was spin coated on top and cured at 200° C. to make the surface layer 14 hydrophobic. A thinner PECVD Si3N4 layer (~100 nm) was deposited and patterned on it to expose the ITO for electrical ground connection, followed by Cytop (~100 nm) deposition. Double-sided tape (~0.1 mm thick; 3M, Inc.) was used as the spacer between the two substrates sandwiching the droplet(s) 16.

Actuation of the droplets 16 was achieved by applying voltage typically of ~70 VAC at 1 kHz to EWOD electrodes 10. Electronic control for the actuation sequence was controlled using LabVIEW software with the help of a digital I/O device. The magnetic force was provided using a cylindrical permanent magnet 12 (NdFeB, 12.7 mm thick and 12.7 mm in diameter) placed on top of the EWOD device. For MBs, Dynal-Invitrogen's Dynabeads were used in two sizes: 4.5 μm (M450 epoxy) and 1.0 μm (MyOne Streptavidin T1) in diameters. Dynabeads have a ferromagnetic core surrounded by a polystyrene shell, often coated with proteins like streptavidin or antibodies, and are, by far, the most commonly used MBs in biological applications like immunoassays and cell separation. To eliminate any other additives present in the MBs' stock solutions, all MBs were washed twice and re-suspended in phosphate-buffered saline (PBS) for EWOD experiments.

FIG. 3A illustrates the initial leftward movement of the droplet 16 toward the magnet 12. As best seen in the magnified portion of FIG. 3A, the MBs are swept off the surface 14 of the device as the meniscus of the droplet 16 moves in the left direction as illustrated by the arrows. The droplet 16 is moved based on actuation of the underlying EWOD electrodes 10 although, as explained herein, other forces may be employed to move the droplet 16. As the droplet 16 moves to the left, the receding meniscus sweeps the MBs off the surface 14 and into the interior portion of the droplet 16 where the strong MB-surface interaction is no longer present. FIG. 3B illustrates additional movement of the droplet 16 in the leftward direction whereby all the MBs are collected under the magnet 12. FIG. 3C illustrates the droplet 16 moving in the opposite (i.e., rightward) direction. Again, the droplet 16 is moved using the underlying EWOD electrodes 10. While the droplet 16 itself moves in the rightward direction, the MBs remain concentrated on the left receding meniscus of the droplet 16 because of the magnetic attraction between the MBs and the magnet 12. With the MBs concentrated on the left side of the droplet 16, the droplet 16 is then split into two droplets 16a, 16b. The result of the splitting process is illustrated in FIG. 3D. The splitting is accomplished by, for example, actuating EWOD electrodes 10a and 10d in FIG. 3D while not actuating the intermediate electrodes 10b, 10c. In this regard, the original droplet 16 is pulled apart or cut into two smaller droplets 16a, 16b. As seen in FIG. 3D, most of the MBs are collected in the left droplet 16a while the right "depleted" droplet 16b is free (or substantially free) of MBs.

FIGS. 4A-4F illustrate a process of using the droplet manipulation method to increase the relative concentration of MBs in a droplet 16 containing a mixture of MBs (represented by dark circles) and non-MBs (represented by light circles). The microfluidic device employing digital EWOD microfluidics is the same as discussed above with respect to FIGS. 3A-3D. In this experiment, the non-MBs were nonmagnetic fluorescent beads (FBs), Nile-red fluorescent (535/575 nm) carboxylate-modified polystyrene microspheres available from Molecular Probes, Inc. (now Invitrogen, Inc.). Exemplary sizes of the non-MBs include 2.0 μm diameter (Fluospheres F8825) and 5.3 μm diameter (Interfacial Dynamics 2-FN-5000). As illustrated in FIG. 4A, when a magnet 12 is introduced over the device, many MBs move toward the magnet 12. However, the non-MBs and some MBs, particularly those touching the surface 14, do not migrate off the surface 14 because of the aforementioned forces. As seen in FIG. 4B, the droplet (16) is then moved leftward and the MBs and non MBs are swept off the surface 14 and re-suspended within the interior of the droplet 16 by the receding meniscus. As seen in FIG. 4C, the MBs are collected by the magnetic force from the magnet 12, but the non-MBs are not. The droplet 16 is moved further to the left until all the MBs and non-MBs on the surface 14 are swept up by the receding meniscus.

FIG. 4D illustrates the droplet 16 moving back to the right side of the magnet 12. As seen in FIG. 4D, the MBs are collected on the left side of the droplet 16 while the non-MBs distribute uniformly across the droplet 16. The droplet 16 is then cut or split using EWOD electrodes 10. For example, EWOD electrodes 10b and 10e may be turned "on" while electrodes 10c and 10d may be turned in the "off" state. The droplet 16 is then cut into two smaller droplets 16a, 16b with most of the MBs remaining in the collected droplet 16a, while the non-MBs are distributed roughly in proportion to volumes of the two cut droplets 16a, 16b. A wash droplet 28 containing buffer can be merged with the droplet 16a and the operations of FIGS. 4B-4E may be repeated. In this manner, the non-MBs can be serially diluted to increase the purity of MBs. For example, only a few cycles of "sweep-and-cut" may be needed to substantially deplete the non-MBs. A particular example of this may be found in Shah et al., "Meniscus-Assisted High-Efficiency Magnetic Collection and Separation for EWOD Droplet Microfluidics," Journal of MEMS, Vol. 18, No. 2, pp. 363-375, April 2009, which is incorporated by reference as if set forth fully herein.

Figure 5B:
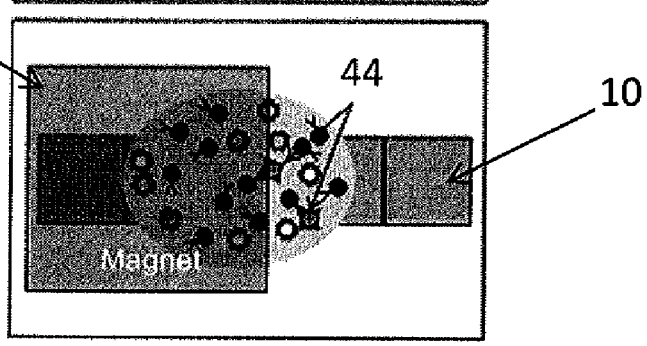
Figure 5C:
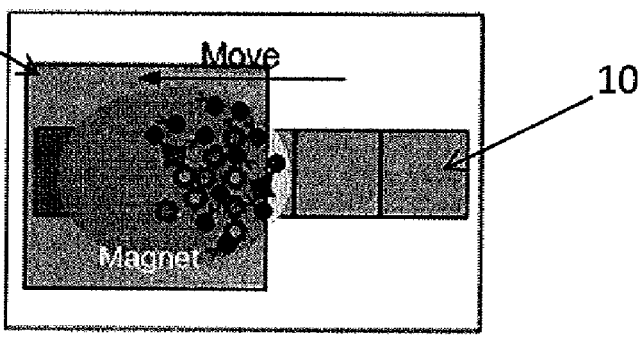
Figure 5D:
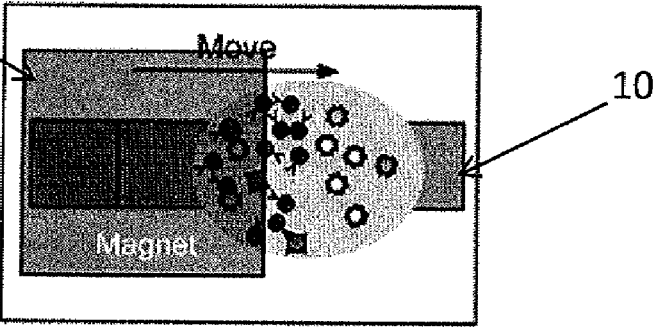
Figure 5E:
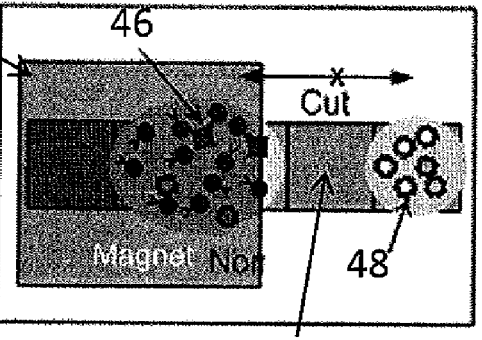

FIGS. 5A-5E illustrate an embodiment of using meniscus-assisted trapping of MBs applied to cell enrichment using a microfluidic device. In this embodiment, as illustrated in FIG. 5A, a droplet 40 containing a mixture of cells that are specific and non-specific (e.g., a particular cell type is a target cell type) is merged with a droplet 42 containing MBs conjugated with antibodies that recognize a specific target cell type. The MBs are allowed to incubate and thus bind to the specific target cells. As seen in FIG. 5B, a magnet 12 is brought into contact with the device (or in the case of an electromagnetic the electromagnet is energized) and the merged droplet containing the MB-cell complexes is moved in the leftward direction. As illustrated in FIGS. 5C and 5D, the meniscus of the merged droplet is then swept first in the leftward direction (FIG. 5C) followed by movement in the rightward direction (FIG. 5D). This process leaves a higher concentration of target cells bound to MBs on the leftmost side of the droplet due to the magnetic attraction to the magnet 12. As seen in FIG. 5E, the droplet is then cut or split at a location that is outside the region of the droplet containing the target cells and bound MBs. The cut droplet 48 thus contains non-target cells, thereby enriching to droplet 46 containing the target cells. This process may be repeated by adding a wash droplet containing a buffer or other solution as previously explained to further improve the enrichment of the target cell types.

FIGS. 6A-6D illustrate another embodiment of a method for enriching the concentration of a target species. The target species may include a specific molecule or cell. In this method, the adhesive forces between the surface 14 and the MBs is reduced by the addition of a surfactant agent. The surfactant agent may include hydrophilic (especially amphipathic) polymers and polymeric surface-acting agents. In particular, the surfactant agent may include non-ionic agents such as polyhydric alcohol-type surfactants like fatty acid esters of glycerol, pentaerythritol, sorbitol, sorbitan, etc., and more hydrophilic agents made by their alkoxylation, including polysorbates (TWEEN®), polyethylene glycol-type surfactants such as PLURONIC surfactants (e.g., poloxamers), polyethylene glycol (PEG), methoxypolyethylene glycol (MPEG), polyacrilic acid, polyglycosides, soluble polysaccharides, dextrins, microdextrins, gums, and agar. In addition, the surfactants could be ionic agents, including anionic surfactants like salts of carboxylic acids (soaps), sulfuric acids, sulfuric esters of higher alcohols, etc., cationic surfactants like salts of alkylamine type, quarternary ammonium salts etc., or amphoteric surfactants like amino acid type surfactants and betaine type surfactants. Once the MBs are at least partially surrounded by these molecules, the MBs that settle to the surface 14 (e.g., under magnetic force, gravity, etc.) have a much weaker adhesion force to the surface 14. The surfactant agent may be pre-coated onto the MB's themselves. Alternatively, the surfactant agent may be added to the solution containing MB's. Thus the fluid forming the various droplets may include the surfactant agent therein. In the latter case, the reduction in adhesive forces is more pronounced if the concentration of the surfactant agent increases. Generally, however, exemplary concentrations for surfactant agents to function effectively can range from below 0.01% (on a weight basis) to over 20% (on a weight basis). As a result, MBs on the surface, which would otherwise not move upon the introduction of the magnet 12, readily do so and can be collected at the desired location.

Thus, unlike the prior method discussed herein, there is no need to move the droplet in a back in forth motion to sweep the droplet meniscus across the MBs to suspend the MBs within the interior portion of the droplet. The addition of the surfactant agent alone is sufficient to reduce the surface forces between the MBs and the surface 14 such that the magnetic forces from magnet 12 are sufficient to cause movement of the MBs off of the surface 14.

Figure 6A:
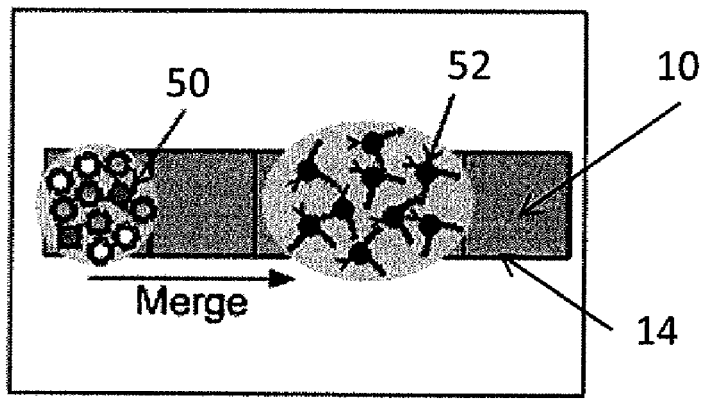
FIGS. 6A-6D illustrate another embodiment of a method for enriching the concentration of a target species. In this embodiment, the target species is a particular cell type. The method is employed using a microfluidic device employing digital microfluidics (e.g., EWOD driving of droplets).
Figure 6B:
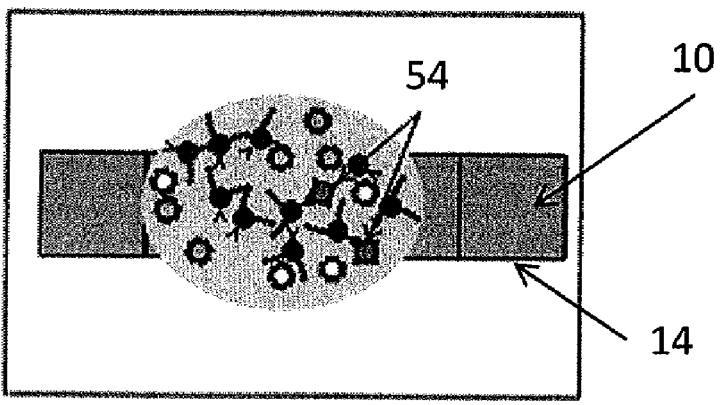

FIGS. 6A-6D illustrates a process of using this method in the context of cellular enrichment. Of course, it should be understood that this method may also apply to the enrichment of other target species such as, for instance, proteins, nucleic acids, etc. FIG. 6A illustrates a droplet 50 containing a mixture of different cell types. The target cells are the square-shaped cells while the non-targets are the circular-shaped cells. This droplet 50 is merged with a droplet 52 containing MBs conjugated with Ab that is selective or recognizes the target cells. Merging of the two droplets 50, 52 is accomplished using the underlying EWOD electrodes 10 although, again, other forces may be employed to move, merge, and cut the various droplets as explained herein. FIG. 6B illustrates the merged droplet 54 along with the incubated complexes formed between the target cells and the MB-Ab. The non-target cells do not bind to the MB-Ab within the droplet. In this example, the droplet 54 itself contains the surfactant agent. The surfactant agent may have been loaded into the original droplet 50 containing the mixture of cells or the droplet 52 containing the MB-Ab (or both droplets 50, 52). Alternatively, the MBs may have been coated with the surfactant agent.

Figure 6C:
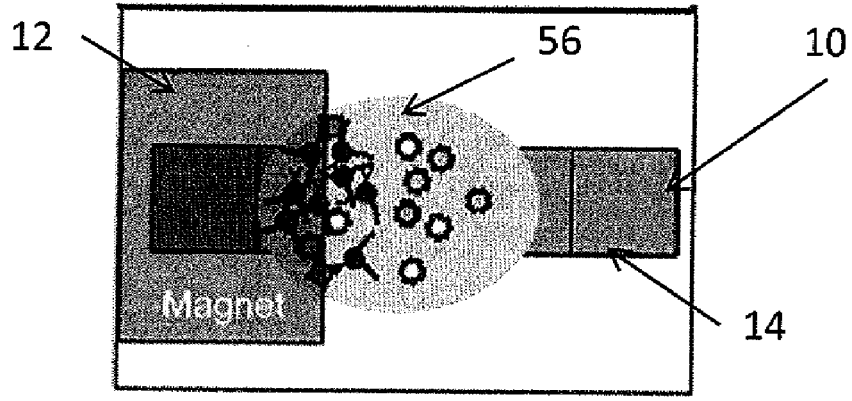
Figure 6D:
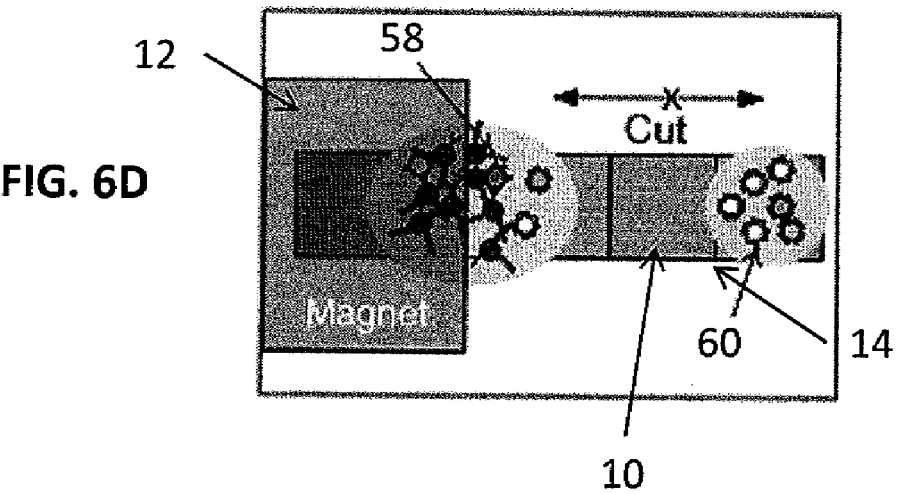

FIG. 6C illustrates a magnet 12 that is placed on one side of the device. The magnet 12 may be a permanent magnet or, alternatively, an electromagnetic. As seen in FIG. 6C, the complexes of the target cells and the MB-Ab are drawn in the leftward direction toward the magnet 12. Because of the addition of the surfactant agent, the MBs located on the surface 14 of the device can be readily lifted off the surface and into the interior portion of the droplet 56. As seen in FIG. 6C, the MBs are concentrated in the left side of the droplet 56 while the non-target cells are distributed within the droplet 56. Next, as seen in FIG. 6D, the droplet 56 is cut or split at a location that is outside the region of the droplet 56 containing the MBs. The droplet 56 is cut using the underlying EWOD electrodes 10 as explained herein. This cut of the droplet 56 forms one droplet 58 that includes an enriched concentration of target cells due to the enrichment of the MBs while the other cut droplet 60 contains non-target cells. As in the prior embodiments, the droplet 58 may be further enriched using a droplet containing a wash buffer or the like (not shown) along with repeating operations illustrated in FIGS. 6C and 6D.

While the embodiment of FIGS. 6A-6D have been described as an independent method of manipulating MBs, it should be understood that the surfactant agent may be used in conjunction with the methods illustrated in FIGS. 2A-2O, 3A-3D, 4A-4F, and 5A-5E. The methods may be independent or complementary as the case may be. It should be noted that the addition of a surfactant agent can affect the wetting properties of the solution. As such, certain operations (like cutting) may require additional droplet manipulation sequences. For instance, an additional droplet free from surfactants may need to be impinged upon the neck region of the stretched droplet so as to help droplet splitting. However, these can still be readily performed on microfluidic platforms including, for instance, the EWOD platform described herein.

For applications where the use of chemical additives is desirable for some other reasons, but where there is no adverse effect of their addition, the method of FIGS. 6A-6D is best suited. For instance, solutions rich in proteins such as albumin and Horse Radish Peroxidase, that typically "foul" the EWOD device, have been effectively actuated using hydrophilic additives. See, e.g., International Publication No. WO 2006/127451, which is incorporated by reference as if set forth herein. In addition, magnetic concentration and separation of, for example, a target nucleic acid (e.g., DNA or RNA) or protein from such a solution could most conveniently be performed using the method of FIGS. 6A-6D.

However, surfactants and hydrophilic polymers are known to affect cellular structure and functioning by influencing the permeability of the cell membrane. Processes involving cells, particularly over any significant length of time, may be influenced by the chemical additives described above with respect to the process of FIGS. 6A-6D. The method that utilizes back and forth movement of a meniscus to sweep MBs off the surface, on the other hand, is a purely physical technique and hence free from such unwanted chemical interference with cellular pathways. For such applications where the chemical additives are undesirable and not otherwise required for microfluidic actuation, it may be desirable to use the moving meniscus technique. Examples of such applications include studies involving yeast, bacteria, and other cells that do not require protein-rich media.

In applications where the presence of surfactants is neither necessary nor detrimental, both techniques are available to use. A potential example of such an application is magnetic separation of DNA and separation of non-biological magnetic and non-magnetic particles. By choosing the appropriate method, these methods can be used for magnetic concentration in droplet-based microfluidics over a wide range of biological and non-biological applications. This includes applications for the collection and separation of nucleic acids, proteins, and cells. The methods described herein extend the scope of digital microfluidics to a range of applications involving target concentration. Performing biochemical assays on a miniature microfluidic chip as opposed to conventional techniques involving bulk fluids has many advantages, including, portability, automation and integration of functions, lower reagent consumption, and shorter reaction times, among others. Droplet microfluidics is an upcoming and promising microfluidics technology where liquids (or gases) are transported in the form of packets or droplets, enabling flexibility and re-programmability of fluid paths. Techniques such as EWOD used for droplet microfluidics employ simple devices with no moving parts (micropumps, microvalves etc.) and consume very little power (<1 mW), making them ideal for portable devices required in point-of-care diagnostic applications. Many such applications require concentration of target analytes, e.g. target proteins in an immunoassay. Separation of specific cells (e.g. CD8+ cells from blood) using specific antibody conjugated magnetic beads is another important application for lab-on-a-chip technology.

Microfluidics-based lab-on-a-chip devices are envisioned as a revolutionary technology for biochemical detection, particularly for quick, low-cost, portable, automated "point-of-care" systems. Droplet microfluidics enabled by EWOD is a simple, low-cost, low-power, and reconfigurable microfluidics technology ideally suited for the above requirements. These methods allow implementation of the MB-based protocols and assays on the droplet-based microfluidic platform, expanding the application window of such affordable, portable and powerful diagnostic devices enabled by droplet microfluidics technologies.

While embodiments of the present invention have been shown and described, various modifications may be made without departing from the scope of the present invention. The invention, therefore, should not be limited, except to the following claims, and their equivalents.

What is claimed is:

1. A method of manipulating magnetic particles disposed within a droplet that is located on or in close proximity to a surface supporting the droplet, the method comprising:
   moving a meniscus of the droplet back and forth so as to lift the magnetic particles off the surface;
   applying a magnetic field to the droplet containing the magnetic particles, the magnetic field concentrating the magnetic particles in a region of the droplet; and
   cutting the droplet at a location outside of the region containing the magnetic particles.

2. The method of claim 1, wherein the magnetic particles comprise magnetic beads.

3. The method of claim 1, wherein the magnetic field is applied by a permanent magnet.

4. The method of claim 1, wherein the magnetic field is applied by an electromagnet.

5. The method of claim 1, wherein the droplet is moved relative to the magnetic field using a plurality of electrodes.

6. The method of claim 1, wherein a surfactant agent is added to the droplet, or the magnetic particles are treated with a surfactant agent, or the surface is treated with a surfactant agent.

7. The method of claim 1, wherein the droplet is surrounded by another liquid.

8. The method of claim 1, wherein the droplet is surrounded by a gas.

9. The method of claim 1, wherein the droplet is moved by using at least one of an electrowetting force, electrostatic force, electromechanical force, electrophoretic force, dielectrophoretic force, electroosmotic force, thermocapillary force, surface acoustic force, or pressure force.

10. The method of claim 1, wherein the magnetic particles comprise magnetic particles conjugated with an antibody.

11. The method of claim 6, wherein the surfactant is selected from the group consisting of polysorbates, poloxamers, polyethylene glycol (PEG), methoxypolyethylene glycol (MPEG), polyacrilic acid, polyglycosides, soluble polysaccharides, dextrins, microdextrins, gums, and agar.

12. The method of claim 1, further comprising merging the cut droplet containing the magnetic particles with a droplet containing a wash or buffer solution.

13. The method of claim 12, further comprising cutting the merged droplet at a location outside of the region containing the magnetic particles.

14. The method of claim 5, wherein the droplet is cut using the plurality of electrodes.

* * * * *